United States Patent [19]
Chappell et al.

[11] Patent Number: 6,068,998
[45] Date of Patent: May 30, 2000

[54] HOST-DERIVED SIGNALS FOR INDUCING ISOPRENOID GENE EXPRESSION AND USES THEREOF

[75] Inventors: Joseph Chappell; Marcos Lusso, both of Lexington, Ky.

[73] Assignee: Board of Trustees of the University Of Kentucky, Administration Building University of Kentucky, Lexington, Ky.

[21] Appl. No.: 08/835,951

[22] Filed: Apr. 11, 1997

Related U.S. Application Data

[60] Provisional application No. 60/015,301, Apr. 12, 1996.

[51] Int. Cl.[7] .............................. C12N 9/00; C12N 5/00
[52] U.S. Cl. ......................... 435/193; 435/410; 435/420; 435/41; 435/193; 424/195.1
[58] Field of Search ..................................... 435/410, 420, 435/41, 193; 424/195.1

[56] References Cited

PUBLICATIONS

Klement, "Hypersensitivity", 8:149–177 (1982).
Keen "Evaluation of the Role of Phytoalexins", 155–177.
Boller, "Chemoperception of Microbial Signals in Plant Cells", *Annu. Rev. Plant Physiol. Plant Mol. Biol.,* 46:189–214 (1995).
Dixon et al., "Early Events in the Activation of Plant Defense Responses", *Annu. Rev. Phytopathol.,* 32:479–501 (1994).
Flor, "Inheritance of Pathogenicity in Melampsora Lini", *Phytopathology,* 32:653–669 (1942).
Schottens–Toma et al., "Purification and primary structure of a necrosis–inducing peptide from the apoplastic fluids of tomato infection with *Cladosporium fulvum* (syn. *Fulvia fulva*)", 33:59–67 (1988).
Renelt et al., "Studies on Elicitor Recognition and Signal Transduction in Plant Defence", *Journal of Experimental Botany,* 44:257–268 (1993).
Lamb, "Plant Disease Resistance Genes in Signal Perception and Transduction", Cell, 76:419–422 (1994).
Bradley et al., "Elicitor– and Wound–Induced Oxidative Cross–Linking of a Proline–Rich Plant Cell Wall Protein: A Novel, Rapid Defense Response", *Cell,* 70:21–30 (1992).
Blein et al., "Responses of Cultured Tobacco Cells to Cryptogein, a Proteinaceous Elicitor from *Phytophthora cryptogea*", *Plant Physiol.,* 95:486–491 (1991).
Sharp et al., "The Primary Structures of One Elicitor–active and Seven Elicitor–inactive Hexa (β–D–glucopyranosyl)–D–glucitols Isolated from the Mycelial Walls of Phytophthora megasperma f. sp. glycinea", *The Journal of Biological Chemistry,* 259:11321–11336 (1984).
Lawrence et al., "The L6 Gene for Flax Rust Resistance is Related to the Arabidopsis Bacterial Resistance Gene RPS2 and the Tobacco Viral Resistance Gene N", *The Plant Cell,* 7:1195–1206 (1995).
Jones et al., "Isolation of the Tomato Cf–9 Gene for Resistance to *Cladosporium fulvum* by Transposon Tagging", *Science,* 266:789–793 (1994).
Knight et al., "Transgenic plant aequorin reports the effects of touch and cold–shock and elicitors on cytoplasmic calcium", *Nature,* 352:524–526 (1991).
Cheong et al., "A Specific, High–Affinity Binding Site for the Hepta–β–glucoside Elicitor Exists in Soybean Membranes", *The Plant Cell,* 3:137–147 (1991).
Cheong et al., "Structure–Activity Relationships of Oligo–β–glucoside Elicitors of Phytoalexin Accumulation in Soybean", *The Plant Cell,* 3:127–136 (1991).
MacKintosh et al., "Protein phosphatase inhibitors activate anti–fungal defence responses of soybean cotyledons and cell cultures", *The Plant Journal,* 5:137–147 (1994).
Milat et al., "Capsidiol and Ethylene Production by Tobacco Cells in Response to Cryptogein, an Elicitor From Phytophthora Cryptogea", *Phytochemistry,* 30:2171–2173 (1991).
Ricci et al., "Structure and activity of proteins from pathogenic fungi Phytophthora eliciting necrosis and acquired resistance in tobacco", *Eur. J. Biochem.,* 183:555–563 (1989).
Grosskopf, et al., "K–252a inhibits the response of tomato cells to fungal elicitors in vivo and their microsomal protein kinase in vitro", *FEBS,* 275:177–180 (1990).
Numberger et al., "High Affinity Binding of A Fungal Oligopeptide Elicitor to Parsley Plasma Membranes Triggers Multiple Defense Responses", *Cell,* 78:449–460 (1994).
Pepper et al., "DET1, a Negative Regulator of Light–Mediated Development and Gene Expression in Arabidopsis, Encodes a Novel Nuclear–Localized Protein", *Cell,* 78:109–116 (1994).
Whitham et al., "The Product of the Tobacco Mosaic Virus Resistance Gene N: Similarity to Toll and the Interleukin–1 Receptor", *Cell,* 78:1101–1115 (1994).
Sharp et al., "The Primary Structures of One Elicitor–active and Seven Elicitor–Inactive Hexa(β–D–glucopyranosyl)–D–glucitols Isolated from the Mycelial Walls of Phytophthora megasperma f. sp. glycinea", *The Journal of Biological Chemistry,* 259:11321–11336 (1984).

(List continued on next page.)

*Primary Examiner*—Leon B. Lankford, Jr.
*Attorney, Agent, or Firm*—Clark & Elbing, LLP

[57] ABSTRACT

Disclosed is a method for preparing a composition that is capable of activating the expression of a gene involved in the synthesis of an isoprenoid, the method involving: (a) contacting a plant cell with an elicitor under conditions that allow an elicitor-induced release of a compound that activates the synthesis of an isoprenoid; and (b) recovering a composition including the compound, wherein the compound is diffusible and has a molecular weight less than or equal to 10,000 daltons. Also disclosed is a substantially pure elicitor-induced composition, the composition being capable of activating a gene involved in the synthesis of a plant isoprenoid.

10 Claims, 4 Drawing Sheets

OTHER PUBLICATIONS

Legrand et al., "Biological function of pathogenesis–related proteins: Four tobacco pathogenesis–related proteins are chitinases", *Proc. Natl. Acad. Sci.,* 84:6750–6754 (1987).

Chappell et al., "Induction of Sesquiterpenoid Biosynthesis in Tobacco Cell Suspension Cultures by Fungal Elicitor", *Plant Physiol.,* 85:469–473 (1987).

Dixon et al., "Phytoalexin Induction in French Bean", *Plant Physiol.,* 71:251–256 (1983).

Viard et al., "Protein Phosphorylation Is Induced in Tobacco Cells by the Elicitor Cryptogein", *Plant Physiol.,* 104:1245–1249 (1994).

Vogeli et al., "Induction of Sesquiterpene Cyclase and Suppression of Squalene Synthetase Activities in Plant Cell Cultures Treated with Fungal Elicitor", *Plant Physiol.,* 88:1291–1296 (1988).

Vogeli et al., "Regulation of a Sesquiterpene Cyclase in Cellulase–Treated Tobacco Cell Suspension Cultures", *Plant Physiol.,* 94:1860–1866 (1990).

Vogeli et al., "Inhibition of Phytoalexin Biosynthesis in Elicitor–Treated Tobacco Cell–Suspension Cultures by Calcium/Calmodulin Antagonists", *Plant Physiol.,* 100:1369–1376 (1992).

Mehdy, "Active Oxygen Species in Plant Defense against Pathogens", *Plant Physiol.,* 105:467–472 (1994).

Graham et al., "Wound–Associated Competency Factors are Required for the Proximal Cell Responses of Soybean to the Phytophthora sojae Wall Glucan Elicitor", *Plant Physiol.,* 105:571–578 (1994).

Facchini et al., "Gene family for an elicitor–induced sesquiterpene cyclase in tobacco", *Proc. Natl. Acad. Sci.,* 89:11088–11092 (1992).

Levine et al., "$H_2O_2$ from the Oxidative Burst Orchestrates the Plant Hypersensitive Disease Resistance Response", *Cell,* 79:583–593 (1994).

Mindrinos et al., "The *A. thaliana* Disease Resistance Gene RPS2 Encodes a Protein Containing a Nucleotide Binding Site and Leucine–Rich Repeats", *Cell,* 78:1089–1099 (1994).

Back et al., "Cloning and Bacterial Expression of a Sesquiterpene Cyclase from Hyoscyamus muticus and its Molecular Comparison to Related Terpene Cyclases", *The Journal of Biological Chemistry,* 270:7375–7381 (1995).

Bent et al., "RPS2 of *Arabidopsis thaliana:* A Leucine–Rich Repeat Class of Plant Disease Resistance Genes", *Science,* 265:1856–1860 (1994).

Baillieul et al., "A new elicitor of the hypersensitive response in tobacco: a fungal glycoprotein elicits cell death, expression of defence genes, production of salicyclic acid, and induction of systemic acquired resistance", *The Plant Journal,* 8:551–560 (1995).

Tavernier et al., "Involvement of Free Calcium in Action of Cryptogein, a Proteinaceous Elicitor of Hypersensitive Reaction in Tobacco Cells", *Plant Physiol.,* 109:1025–1031 (1995).

Martin et al., "Map–Based Cloning of a Protein Kinase Gene Conferring Disease Resistance in Tomato", *Science,* 262:1432–1436 (1993).

Staskawicz et al., "Molecular Genetics of Plant Disease Resistance", *Science,* 268:661–667 (1995).

Song et al., "A Receptor Kinase–Like Protein Encoded by the Rice Disease Resistance Gene Xa21", *Science,* 270:1804–1806 (1995).

Felix et al., "Rapid changes of protein phosphorylation are involved in transduction of the elicitor signal in plant cells", *Proc. Natl. Acad. Sci.,* 88:8831–8834 (1991).

Chappell et al., "Characterization of a Diffusible Signal Capable of Inducing Defense Gene Expression in Tobacco", *Plant Physiology,* 113:621–629 (1997).

HOST-DERIVED SIGNALS FOR INDUCING ISOPRENOID GENE EXPRESSION AND USES THEREOF

CROSS REFERENCE TO RELATED APPLICATIONS

This application claims benefit from provisional application 60/015,301 filed Apr. 12, 1996.

STATEMENT AS TO FEDERALLY SPONSORED RESEARCH

This invention was made in part with Government finding, and the Government therefore has certain rights in the invention.

BACKGROUND OF THE INVENTION

Models for the mechanisms underlying plant-patiogen interactions have typically involved host-specific receptors that recognize pathogen-specific ligands released from the invading pathogen (Dixon et al., *Annu. Rev. Phytopathiol* 32:479–501, 1994; Lamb, *Cell* 76:419–422, 1994; Boller, *Annu. Rev. Plani. Phzysiol. Plant Mol. Biol.* 46:189–214, 1995). This signal transduction pathway then leads to the induction of a broad repertoire of host defense responses, including phytoalcxin biosynthesis (Keen, In: *Plant Disease Control*, R. C. Staple, ed, John Wiley & Sons, New York, pp. 155–177, 1981), the synthesis and secretion of hydrolytic enzymes (Kombri et al., *Proc. Natl. Acad. Sci. USA* 84:6750–6754, 1988), the rigidification of the plant cell wall (Bradley et al., *Cell* 70:21–30, 1992), and the activation of a developmental program for localized cell death. When successful, these responses ultimately arrest the growth of the invading microorganism.

In addition to pathogen-specific signals that induce host defense gene expression, there have been a number of reports suggesting that diffusible or transmissible host-derived signals are involved in orchestrating plant defense responses. For example, Dixon et al. (*Plant Physiol.* 71:251–256, 1983) have reported that denatured RNase was capable of inducing the release of a low molecular weight soluble factor that activates phenylpropanoid biosynthetic enzymes and phytoalexin accumulation in both soybean hypocotyls and cell suspension cultures. Graham and Graham (*Plant Phzysiol.* 105:571–578, 1994) have also reported that a transmissible signal, referred to as an elicitation competency factor, was released from wounded cells and was found to induce and enhance cellular responses to wounding in proximal or (closely neighboring cells. In addition, $H_2O_2$ has been identified as a diffusible signal that is capable of selectively triggering the induction of a sub-class of host defense genes (Levine et al., *Cell* 79:583–593, 1994).

SUMMARY OF THE INVENTION

In general, the invention features a method for preparing a composition that is capable of activating expression of a gene involved in the synthesis of an isoprenoid (e.g., a plant isoprenoid), for example, an elicitor-induced composition produced as described herein. In one embodiment, the method involves: (a) contacting a plant cell with an elicitor under conditions that allow an elicitor-induced release of a compound that activates the synthesis of an isoprenoid; and (b) recovering a composition including that compound, wherein the compound is diffusible and has a molecular weight less than or equal to 10,000 daltons. In preferred embodiments, the compound is diffusible and has a molecular weight less than or equal to 1,000 daltons; the composition is recovered by dialysis; and release of the compound is induced by the elicitor known as cryptogein.

In a related aspect, the invention features a substantially pure composition produced according to the above method.

In another related aspect, the invention features a substantially pure composition, the composition being capable of activating the expression of a gene involved in the synthesis of an isoprenoid, such as a plant isoprenoid. In preferred embodiments, the composition includes a compound that is: less than or equal to 10,000 daltons (and preferably less than or equal to 1,000 daltons); heat stable at a temperature between 75–80° C. for 15 minutes; stable to a freeze-thaw cycle; stable to lyophilization; not readily soluble in an organic solvent; and/or capable of activating sesquiterpene synthase activity (for example, epi-5-aristolochene synthase activity) in a plant cell.

By "isoprenoid" is meant a compound that is derived from an isoprene building block. In particular, isoprenoid compounds include, without limitation, monoterpenes, diterpenes, sesquiterpenes, and sterols. As referred to herein, the term "plant isoprenoid" means that the isoprenoid compound is found in a plant, but should not be construed to exclude isoprenoids that are also found in other organisms, for example, animal, fungal, or bacterial sources.

By "elicitor" is meant any molecule produced by i pathogen that is capable of initiating a plant defense response. Examples of elicitors include, without limitation, one or more toxic ions, e.g., mercuric ions, other chemically defined compositions, metabolic inhibitors, cell wall glycans, C-glycosidic elicitors (e.g., Midland et al. *J Organic. Chemistry* 58:2940; Smith et al. *Tetrahedron Letters* 34:223, 1993), certain glycoproteins, certain enzymes, fungal spores, chitosans, and elicitins (for example, harpin, cryptogein, and pariscein).

By "elicitin" is meant a protein elicitor, such as that described, for example, by Yu et al., *Proc. Natl. Acad. Sci. USA* 92:4088–4094, 1995.

By "elicitor-induced composition" is meant a composition that is obtained from a plant cell following contact of that cell with an elicitor.

By "substantially pure elicitor-induced composition" is meant a composition (for example, the ECM composition described herein) which has been separated, at least in part, from the components which naturally accompany it. Typically, the composition is substantially pure when it is purified at least 100-fold, preferably, 200-fold, more preferably, 300-fold, and most preferably 400-fold from the compounds and naturally-occurring organic molecules with which it is naturally associated. A substantially pure elicitor-induced composition may be obtained, for example, according to the methods disclosed herein (for example, from a plant cell). Purity can be measured by any appropriate method, for example, by using the standard methods of chromatography such as high performance liquid chromatography (HPLC).

Other features and advantages of the invention will be apparent from the following description of the preferred embodiments thereof.

DETAILED DESCRIPTION

The drawings will first be described.

Drawings

FIG. 5 is a schematic illustration showing that ECM does not regulate the production of an additional diffusible secondary signal. MS medium or ECM samples (5 ml), with or without 5 ml of tobacco cell suspension cultures sealed in dialysis tubing were incubated in 25 ml of external MS medium. One ml aliquots of the external MS medium was removed after three, six, and twelve hours of incubation, concentrated by lyophilization, and half of the resuspended samples were tested for the ability to induce sesquiterpene synthase in a tobacco cell suspension culture.

There now follows a description of a series of experiments reporting the isolation and characterization of a diffusible, host-derived signalling compound that activates isoprenoid synthase gene expression. This example is provided for the purpose of illustrating the invention, and should not be construed as limiting.

Figure 1:
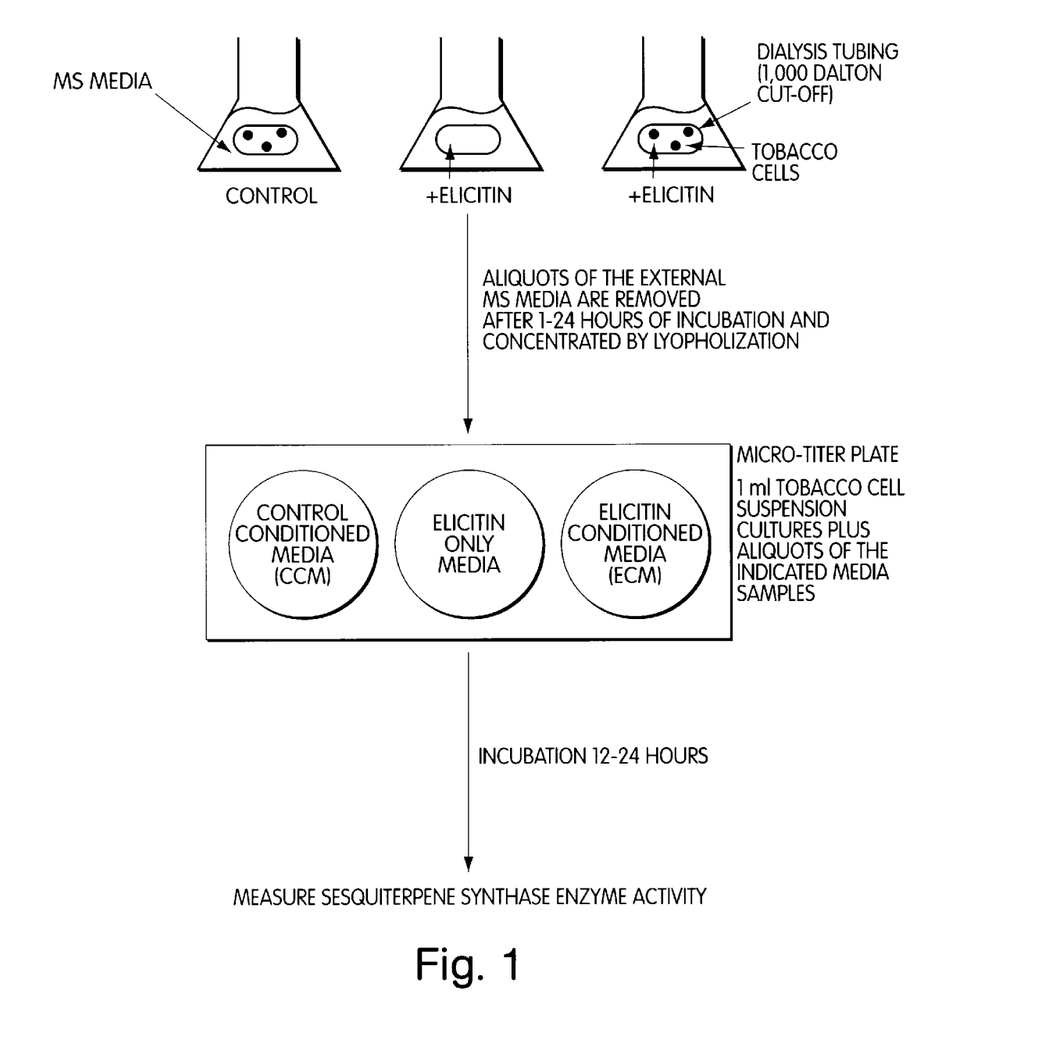
FIG. 1 is a schematic illustration showing the steps involved in a bioassay for determining whether a secondary, host-derived signal is capable of triggering the induction of a isoprenoid biosynthetic enzyme. Tobacco cells incubated, with and without cryptogein elicitin, in Murashige-Skoog (MS) medium-n are sealed in dialysis tubing (1,000 dalton cut-off) for various time periods and are incubated in an external MS medium. Samples of the external MS medium are subsequently collected, concentrated by lyophilization, and evaluated for the presence of a molecule that is capable of inducing sesquiterpene synthase enzyme activity in freshly prepared tobacco suspension cell cultures.

Bioassay for Secondary Signals Capable of Inducing Sesquiterpene Synthase Enzyme Activity in Tobacco Cells The experimental strategy used to investigate the release of a diffusible, host-derived signal from elicitor-challenged tobacco cells is shown in FIG. 1. Conditioned media samples were prepared as follows: 2 ml of cells, 2 ml of MS medium containing 0.5 μg elicitin (elicitin-only medium), or 2 ml of cells (CCM) and 0.5 μg of elicitin (ECM) were sealed in dialysis tubing with a 1,000 dalton cut-off, and each sample was incubated individually in 20 ml of external MS medium for sixteen hours. Samples of external MS medium from each treatment were then concentrated 8-fold by lyophilization, and 50 μl aliquots (corresponding to 1/50 of the original 20 ml media samples) were tested for the ability to induce sesquiterpene synthase in a second incubation with 1 ml of tobacco cell suspension cultures.

Results from these assays are shown in Table I (below). Tobacco cells incubated in MS medium alone were found to contain undetectable levels of sesquiterpene synthase enzyme activity. Sesquiterpene synthase activity, however, was found to be induced in cells treated directly with elicitin protein. To determine the presence of a diffusible signal, control-conditioned medium (CCM) (i.e., external MS medium resulting from incubating tobacco cells sealed within the dialysis tubing in MS medium) was found not to induce sesquiterpene synthase activity. In contrast, elicitin-conditioned medium (ECM) (i.e., external MS medium resulting from incubating tobacco plus elicitin protein within the dialysis tubing in MS medium) was found to induce sesquiterpene synthase activity to a similar extent as When the cryptogein elicitin protein was added directly to the cells. The induction of synthase activity by ECM was not due to some low molecular weight, diffusible component within the elicitin preparation because the elicitin-only medium (i.e., external MS medium resulting from incubating an aliquot of the elicitin protein within the dialysis tubing in MS medium) did not induce significant synthase activity.

TABLE I

| Treatment | Enzyme Activity (nmole/h · mg protein) |
| --- | --- |
| None (control cells only, negative control) | 1.3 |
| Elicitin (0.1 μg/ml, positive control) | 54.7 |
| Control-conditioned media (CCM) | 2.0 |
| Elicitin-only media | 4.3 |
| Elicitin-conditioned media (ECM) | 52.8 |

Dose-Dependent Induction of Sesquiterpene Synthase Enzyme Activity in Tobacco Cell Suspension Cultures by ECM To evaluate whether induction of sesquiterpene activity was dose-dependent, tobacco cell suspension cultures were incubated with various amounts of elicitin or ECM. Conditioned media samples were prepared as follows: 20 ml of cells alone or 20 ml of cells containing 8 μg of elicitin were sealed in dialysis tubing with a 1,000 dalton cut-off and were incubated in 50 ml of MS medium for sixteen hour. Samples of the external MS medium were then concentrated 5-fold by lyophilization, and aliquots corresponding to 1/200th, 1/50th, and 1/25th of the original 50 ml samples were evaluated for the ability to induce sesquiterpene synthase in tobacco cell suspension cultures. Control assays included incubations of 4 ml of tobacco cell suspension cultures with appropriate amounts of MS medium (i.e., MS only), and cells incubated with 0.5 μg/ml of elicitin and the appropriate amounts of MS medium (i.e., MS plus elicitin).

As shown in Table II (below), ECM induction of sesquiterpene synthase activity in tobacco cells was observed to be dose-dependent. Maximal induction of synthase activity was typically observed with the equivalent of 1/25th to 1/50th of the external MS medium. This calculation assumes a standardized volume ratio of external media to cells sealed within the dialysis tubing of 2.5:1, respectively. However, ratios of 5:1 to 10:1 of external media to volume of sealed cells appeared to represent a more efficient extraction of the diffusible secondary signal.

TABLE II

Sesquiterpene Synthase Enzyme Activity (nmole/h · mg protein)

| Aliquot | MS only | MS plus elicitin | CCM | ECM |
|---|---|---|---|---|
| 50 µl | 2.8 | 36.5 | 0.8 | 3.0 |
| 200 µl | 2.0 | 40.9 | 0.8 | 20.8 |
| 400 µl | 2.0 | 42.9 | 1.4 | 31.6 |

Figure 2:
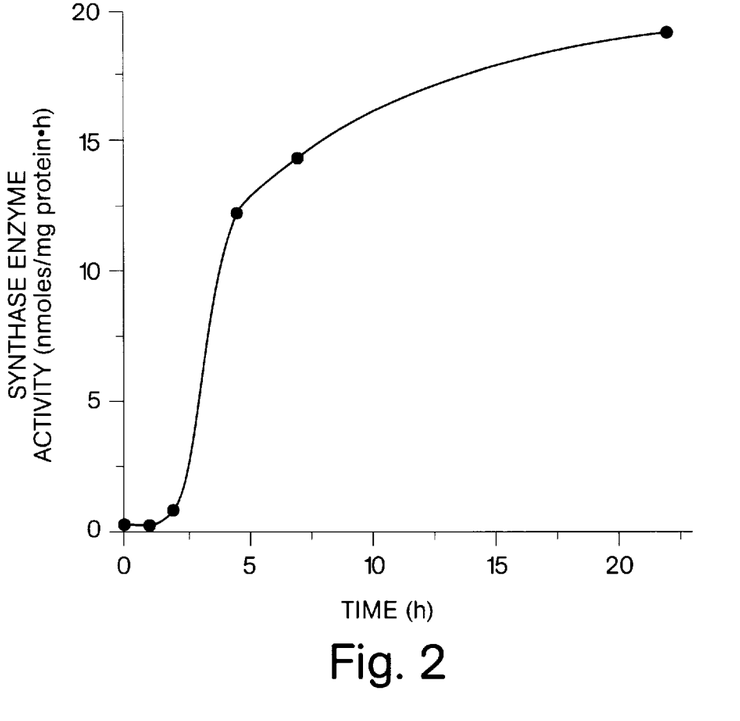
FIG. 2 is a graph showing the time course for the release of a diffusible secondary signal from tobacco cells. 10 ml of tobacco cell suspension culture plus 4 μg of elicitin were sealed in dialysis tubing and incubated in external MS media Samples of the external MS medium were collected at the times indicated, concentrated 6-fold by lyophilization, and aliquots corresponding to 1/20th of the collected samples were tested for its ability to induce sesquiterpene synthase activity in a tobacco cell suspension culture.

As shown in FIG. 2, the release of a diffusible signalling compound from tobacco cell cultures was time-dependent, with approximately ½ of the maximum diffusible signalling component being released within four hours of initiating the elicitin-treatment. A slower release of additional secondary signal factor over the next twenty hours was also observed.

The Diffusible Compound is Resistant to Select Hydrolases

To determine the chemical nature of the signalling; compound, the sensitivity of ECM to several hydrolytic enzymes was evaluated. Hydrcolytic enzymes (i.e., *Aspergillus oiyzae* Type II protease, Rhizobus sp. pectinase, bovine pancreatic RNase A, and DNase I) were prepared at an initial concentration of 10 mg/ml and dialyzed overnight in 1,000 dalton cut-off tubing. Aliquots of the hydrolases corresponding to 5 mg were then incubated with 1 ml of ECM for two to four hours. The ECM-hydrolase mixtures were dialyzed a second time in a 1,000 dalton cut-off dialysis tubing against 5 ml of $H_2O$. Samples of external $H_2O$ were collected, lyophili?ed, resuspended in a final volume of 100 µl, and each sample was incubated with tobacco cell suspension cultures for sixteen hours before determining sesquiterpene synthase enzyme activity.

Treatment of ECM with protease, pectinase, RNase, or DNase did not destroy the ECM's ability to induce synthase activity (Table III), indicating that either the factor was resistant to these enzymes or was not a protein- or pectin-containing factor, or a RNA or DNA factor. The diffusible compound was also not likely to be $H_2O_2$ or a related activated oxygen species, because neither treatment of the ECM with catalase nor lyophilization of the ECM diminished synthase inducing activity; both treatments would be expected to eliminate $H_2O_2$ or related oxygen radicals from the ECM (data not shown). Consistent with this notion, direct addition of $H_2O_2$ at a wide range of concentrations to the cell cultures did not induce synthase activity. In addition the diffusible signal appeared not to be hydrophobic because it did not partition into organic solvents such as chloroform or hexane; ECM's ability to activate sesquiterpene activity was also not altered by these treatments.

TABLE III

| Treatment | Enzyme Activity (nmole/h · mg protein) |
|---|---|
| None | 0.5 |
| ECM | 54.0 |
| ECM + protease | 49.4 |
| ECM + pectinase | 44.9 |
| ECM + RNase | 32.5 |
| ECM + DNase | 38.6 |

The Diffusible Signal as a Primary Inducer

The diffusible signal could represent either a primary inducer (i.e., an integral component of a signal transduction chain operating to induce the complete repertoire of defense responses) or the signal could represent a secondary message (i.e., a component of relative low efficiency and specificity for inducing defense responses which might be released non-specifically from necrotizing cells). If the diffusible factor is a primary inducer, then the intrinsic activity of the factor to induce sesquiterpene synthase enzyme activity and other defense responses would be expected to be greater than the elicitin protein itself To distinguish between these possibilities, the induction time course of sesquiterpene synthase activity was determined using optimal amounts of ECM and elicitin.

Figure 3:
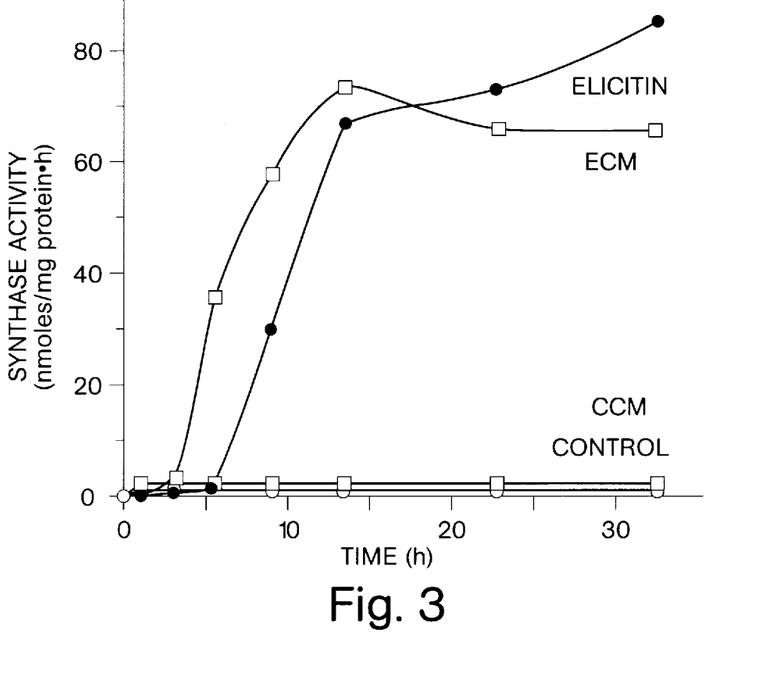
FIG. 3 is a graph showing a comparison of the induction time course of sesquiterpene synthase in tobacco cell suspension cultures treated with either elicitin or elicitin-conditioned medium. Sesquiterpene enzyme activity was measured in extracts prepared from control cultures (shown as open circles), cultures receiving control-conditioned medium (CCM, shown as open squares), elicitin-conditioned media (ECM; shown as closed squares), or elicitin (0.1 μg/ml) (shown as closed circles). Conditioned media samples (CCM or ECM) were added at a concentration corresponding to 1/20th of the collected sample of external MS medium.

As shown in FIG. 3, ECM treatment caused a significantly more rapid induction of synthase activity than elicitin-only treatment, with half maximal activity occurring five to six hours after initiation of ECM treatment, and 10 or more hours after initiation of elicitin-only treatment. Both ECM and elicitin-only treatments, however, induced synthase activity to the same maximum activity level by fourteen to fifteen hours after treatment initiation.

Figure 4A:
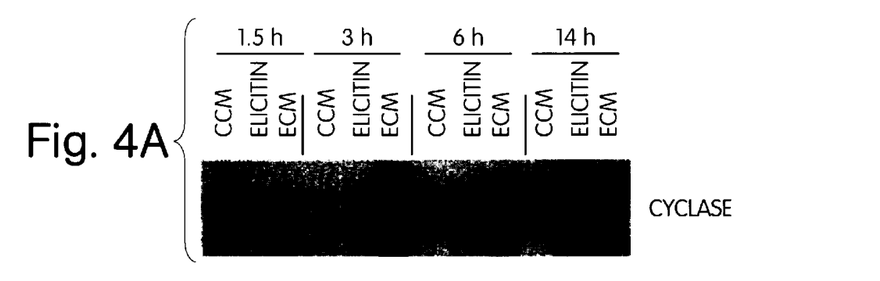
FIGS. 4A, 4B, 4C, 4D, and 4E are photographs of RNA blots showing the induction of plant defense gene expression in tobacco cell suspension cultures that were treated with ECM. The blots were hybridized using the following gene probes: sesquiterpene synthase (FIG. 4A), acidic chitinase (FIG. 4B), basic chitinase (FIG. 4C), PR1 (FIG. 4D), and Hsr203 (FIG. 4E).
Figure 4B:
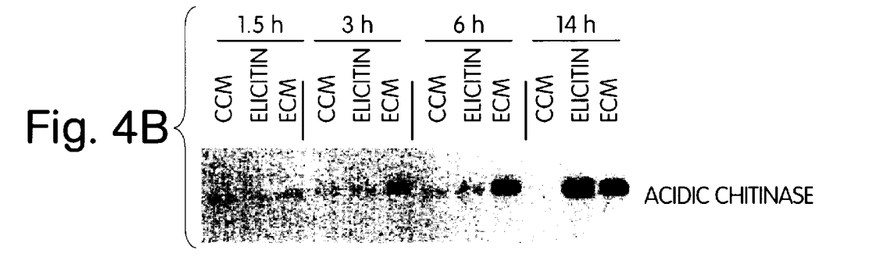
Figure 4C:
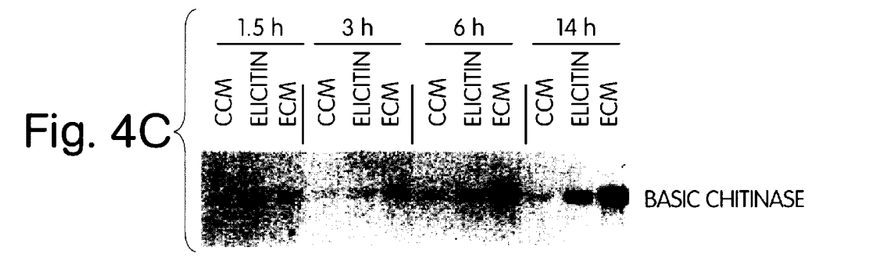

The differential induction time courses of synthase activity by ECM and elicitin also extended to steady-state measurements of the synthase mRNA (FIG. 4A). Elicitin-induced synthase mRNA was first observed three to six hours after initiation of treatment, and level of synthase mRNA appeared to accumulate throughout the fourteen hour experiment. In comparison, ECM treatment induced a rapid accumulation of synthase mRNA, with a maximum accumulation of mRNA occurring approximately three hours after initiation of treatment (FIG. 4A). After three hours, the level of synthase mRNA declined. Elicitor and elicitin treatments are normally associated with the induction of several other defense genes including PR proteins and hydrolyases such as chitinase and glucanase.

Figure 4D:
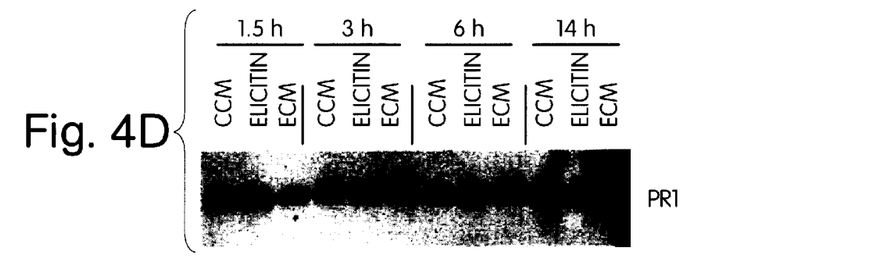
Figure 4E:
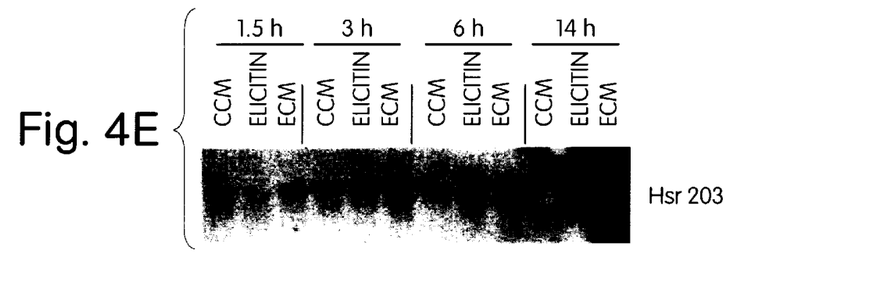

To evaluate the spectrum of defense genes induced by ECM, the gene induction patterns of chitinase, PR1, and Hsr203 were determined and compared to the induction patterns by elicitin treatment (FIGS. 4B–4E). ECM treatment induced both acidic and basic chitinase more rapidly than did elicitin treatment (FIGS. 4B and 4C), although the induction time courses were delayed significantly relative to that for the synthase mRNA. PR1 mRNA was easily detected in control cell cultures, and there appeared to be little if any modulation of this mRNA level by either ECM or elicitin-treatments (FIG. 4D). Hsr203 mRNA was also detectable in control cell cultures, but the level of its expression was induced by both ECM and elicitin-treatments (FIG. 4E). Based, however, on the relative intensity of the hybridization signal, the ECM treatment induced a greater accumulation of Hsr203 mRNA than elicitin-treatment.

The Diffusible Signal Does Not Regulate the Release of an Additional Signal

Figure 5:
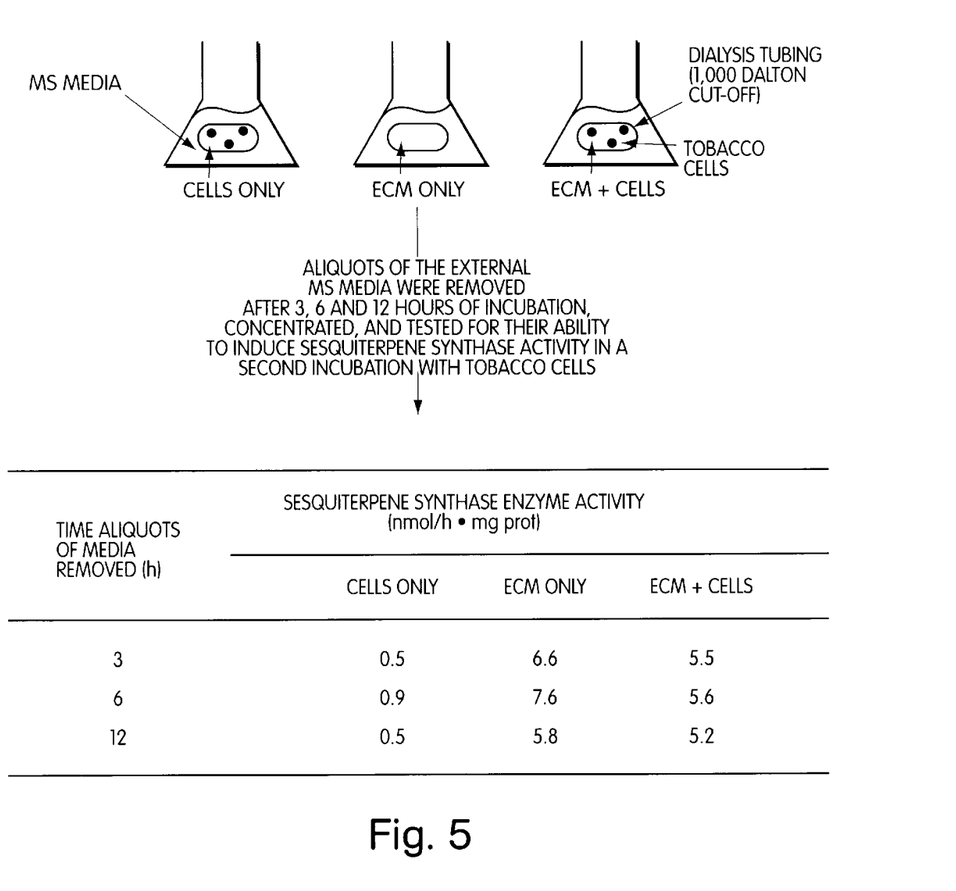

If the diffusible signal found in ECM served as a means of warning neighboring cells of a pathogen attack, then it might also stimulate the release of additional diffusible signals from the cells it contacts. To evaluate this possibility, the release of diffusible factors from cells sealed in 10,000 dalton cut-off tubing containing ECM were compared to the release of diffusible factor from only ECM sealed in the dialysis tubing (FIG. 5). The results indicated that the majority of the diffusible factor was released from the ECM-only sample within the first three hours of the experiment. A slightly lower level of diffusible signal was released from the ECM-plus-cells treatment also within this time frame. No additional diffusible factor was detected in the ECM-plus-cells samples at the later time points, indicating that the diffusible signal does not itself induce the release of other signal molecules.

The experiments described above were carried out using the following techniques.

Cell Cultures and Experimental Treatments

Cell suspension cultures of *Nicotiana tabacum* cv. Kentucky 14 were maintained in Murashige-Skoog (MS) media, subcultured weekly, and their growth monitored by measuring the increase in fresh weight as described by Chappell and Nable (*Plant Physiol.* 85:469–473, 1987). Cultures in the rapid phase of growth were used for all experiments presented above. Induction treatments were routinely performed in 12-well tissue culture plates containing 1 ml aliquots of cell suspension culture per well. Elicitor treatment was initiated by the addition of 0.1 to 0.5 μg of the cryptogein elicitin protein of Phytophthora cryptogea per ml of cell suspension culture (Blein et al. *Plant Physiol.* 95:486–491, 1991). Cells were harvested by vacuum filtration and stored frozen in liquid nitrogen until analyzed. To assay for a diffusible, secondary host-derived signal, aliquots of a tobacco cell suspension culture, with and without cryptogein elicitin protein, were sealed inside a 1,000 dalton molecular weight cut-off dialysis membrane (Spectra/por). The dialysis tubing was then incubated with shaking in MS medium, and at various time periods samples of the external MS medium were collected and lyophilized. Lyophilized samples were resuspended with sterile water at a 5 to 10 fold higher concentration then the collected samples and used directly in subsequent incubation assays of sesquiterpene synthase in tobacco cultures as described above.

Sesquiterpene Synthase Enzyme Assay

Frozen tobacco cells were homogenized in 400 to 800 μl of 80 mM potassium phosphate buffer (pH 7.0), 20% glycerol, 10 mM sodium metabisulfite, 10 mM sodium ascorbate, 15 mM magnesium chloride, and 5 mM DTT with a mechanical homogenizer designed for use with eppendorf tubes, and the resulting sluny was centrifuged for ten minutes at 12,000 g in a microfuge. The synthase assay was p)performed by incubating 5 to 10 μl aliquots of the supernatant (5–25 μg total protein), 1.5 nmoles of [$^3$H]FPP (87 μCi/μmol), and sufficient reaction buffer (0.5M Tris 7.5, 0.2M $MgCl_2$) to bring the final volume to 50 μl for thirty minutes at 37° C. before extraction with 150 μl n-hexane. The hexane phase was then reacted against silica powder to bind any farnesol generated by phosphatase activity. Radioactivity in an aliquot (50 μl) of the hexane phase was then determined according to standard methods. The sesquiterpene synthase activity was expressed as nmoles of cyclic product formed per hour per mg protein. The absolute structure of the sesquiterpene product was previously described as 5-epi-aristolochene by Whitehead and Threlfall (1992).

RNA Blots

Total cellular RNA was extracted and hybridized as described by Pepper et al. (*Cell* 78:109–116, 1994). Hybridization probes were tobacco sesquiterpene synthase cDNA (Back and Chappell, *J. Biol. Chem.* 270:7375–7381 (1995)), acidic and basic chitinase (see, for example, Lawton et al., *Plant Mol. Biol.* 19:735–743), PR1 (see, for example, Payne et al., *Plant Mol. Biol.* 11:89–94, 1988), and HSR203 (see, for example, Pontier et al., *Plant J.* 5:507–521, 1994).

Characterization

Further analysis of a substantially pure elicitor-induced composition (for example, ECM) is accomplished through the use of conventional purification methods. For example, further characterization and fractionation of the composition is performed using techniques such as chromatography (e.g., ion-exchange molecular weight sizing gel filtration, HPLC, or RP-HPLC), gas chromatography (GC), GC-mass spectroscopy, or other spectroscopic methods such as infrared and nuclear maunetic resonance spectroscopies. In addition, other properties of the elicitor-induced compositions of the invention may be determined using a variety of hydrolytic enzymes (for example, cellulase, polygalacturonase, pectinase, pectolyase, chitinase, glucanase, proteases, or proteinases) as well as standard acid-base hydrolyses under an assortment of standard conditions.

Use

The invention described herein is useful for a variety of agricultural and commercial purposes including, but not limited to, controlling, modulating, or regulating gene expression (e.g., of a pharmaceutically useful compound), increasing crop yields, improving crop and ornamental quality, and reducing agricultural production costs. The methods of the invention provide a simple means for preparing substantially pure compositions that are capable of activating genes involved in the synthesis of any of a number of isoprenoid compounds (for example, metabolites such as sterols, carotenoids, growth regulators, and the polyprenol substituents of dolichols, quinones, and proteins; monoterpenes; diterpenes; and sesquiterpenes). By activating, these genetic pathways, the compositions modulate a variety of biological functions including, without limitation, maintenance of membrane integrity, photoprotection, and defense-related interactions. Thus, the methods described herein have agricultural value for the preparation of compositions that are useful as plant protectants.

Such elicitor-induced compositions may be prepared from a variety of plants including, without limitation, tree species, ornamental species, temperate fruit species, tropical fruit species, vegetable species, legume species, monocots, dicots, or any plant of commercial or agricultural significance. Particular examples of suitable plants include, but are not limited to, Conifers, Petunia, Tomato, Potato, Tobacco, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Rice, Maize, Millet, Onion, Barley, Orchaid grass, Oat, Rye, and Wheat.

For agricultural purposes, the elicitor-induced compositions or agents identified using the methods disclosed herein are useful as chemicals applied as sprays or dusts on the foliage of plants. Typically, such agents are administered to the surface of the plant prior to pathogen attack to prevent infection. Seeds, bulbs, roots, tubers, and corms may also be treated to prevent pathogenic attack after planting by controlling pathogens carried on them or existing in the soil at the planting site. Soil to be planted with vegetables, ornamentals, shrubs, or trees can also be treated with elicitor-induced composition as fumigates for control of a variety of microbial pathogens. Treatment is preferably done several days or weeks before planting. The compositions of the invention can be applied by a standard mechanized route, for example, a tractor, or by hand application.

The compositions of the invention are also useful for promoting or improving a variety of plant characteristics including photoprotection or synthesis of growth regulators or plant pigments.

All publications mentioned in this specification re herein incorporated by reference to the same extent as if each individual publication was specifically and individually indicated to be incorporated by reference.

Other Embodiments

From the above description, it will be apparent that variations and modifications may be made to the invention described herein to adopt it to various usages and conditions.

What is claimed is:

1. A method for preparing a composition that is capable of activating sesquiterpene synthase gene expression, said method comprising:
   (a) contacting a plant cell selected from the group consisting of a tobacco cell, a tomato cell, and a potato cell with an elicitin under conditions and with an amount that induces said cell to produce a composition that activates sesquiterpene synthase gene expression in a tobacco cell; and
   (b) recovering said elicitin-induced composition.

2. The method of claim 1, wherein one of said compounds is diffusible and has a molecular weight less than or equal to 1,000 daltons.

3. The method of claim 1, wherein said composition is recovered by dialysis.

4. A composition produced according to the method of claim 1.

5. The method of claim 1, wherein said composition comprises one or more compounds that are diffusible and have a molecular weight less than 10,000 daltons.

6. The method of claim 1, wherein said elicitin is cryptogein.

7. The method of claim 1, wherein said sesquiterpene synthase is epi-5-aristolochene synthase.

8. A substantially pure composition derived from a plant cell selected from the group consisting of a tobacco cell, a tomato cell, and a potato cell, said composition being capable of activating sesquiterpene synthase gene expression in a tobacco cell, wherein said composition comprises the following attributes:
   (i) said composition is capable of activating said sesquiterpene synthase gene expression in said tobacco plant cell after being treated with orotease, pectinase, DNase, or RNase;
   (ii) said composition is capable of activating said sesciuiterpene synthase gene expression in said tobacco plant cell after being lyophilized and reconstituted;
   (iii) said composition does not partition into the organic phase following extraction with hexane; and
   (iv) said composition comprises a compound having a molecular weight less than or equal to 10,000 daltons.

9. The composition of claim 8, wherein said compound has a molecular weight less than or equal to 1,000 daltons.

10. The composition of claim 8, wherein said sesquiterpene synthase is epi-5-aristolochene synthase.

* * * * *